(12) United States Patent
Atkinson et al.

(10) Patent No.: US 8,427,638 B2
(45) Date of Patent: Apr. 23, 2013

(54) OPTICAL MEASUREMENT DEVICE INCLUDING A MULTI-COMPONENT SEALING ASSEMBLY

(75) Inventors: Robert Atkinson, Richmond, TX (US); Christopher M. Jones, Houston, TX (US); Michael T. Pelletier, Houston, TX (US); Nathan Harder, Magnolia, TX (US); Robert J. Murphy, Kingwood, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 13/574,991

(22) PCT Filed: Jan. 21, 2011

(86) PCT No.: PCT/US2011/022104
§ 371 (c)(1),
(2), (4) Date: Jul. 24, 2012

(87) PCT Pub. No.: WO2011/094134
PCT Pub. Date: Aug. 4, 2011

(65) Prior Publication Data
US 2012/0300200 A1    Nov. 29, 2012

Related U.S. Application Data

(60) Provisional application No. 61/298,805, filed on Jan. 27, 2010.

(51) Int. Cl.
*G01N 1/10* (2006.01)
(52) U.S. Cl.
USPC .................................. 356/246; 356/241.1
(58) Field of Classification Search ............... 356/241.1, 356/244, 246
See application file for complete search history.

(56) References Cited

U.S. PATENT DOCUMENTS

| 4,552,368 | A |   | 11/1985 | Wallace |
| 4,588,893 | A | * | 5/1986 | Vidrine et al. ................. 250/428 |

(Continued)

FOREIGN PATENT DOCUMENTS

| WO | WO-2011094134 A2 | 8/2011 |
| WO | WO-2011094134 A3 | 8/2011 |

OTHER PUBLICATIONS

"Application Serial No. PCT/US2011/022104, International Search Report mailed Aug. 19, 2011", 3 pgs.

(Continued)

*Primary Examiner* — Tarifur Chowdhury
*Assistant Examiner* — Michael P Lapage
(74) *Attorney, Agent, or Firm* — Schwegman Lundberg & Woessner, P.A.

(57) ABSTRACT

Optical measurement devices including one or more sealing assemblies are described. The sealing assemblies are configured for use at relatively high temperatures and pressures, such as temperatures over 200 degrees F. and pressures over 10,000 psi. The sealing assemblies can include a deformable seal element surrounded on each side by a backup seal element. In some examples, the deformable seal element is formed of a material selected from a group consisting of a fluoroelastomer or polytetrafluoroethylene, and the backup seal elements are formed of a material selected from a group consisting of flexible graphite or metal foil. Optionally, at least one additional seal element functioning as an extrusion barrier can be placed on the opposite side of one or both backup seal elements from the deformable seal element. The additional seal element can be formed of polyether ether ketone or flexible graphite, for example. Additional devices and assemblies are described.

22 Claims, 3 Drawing Sheets

U.S. PATENT DOCUMENTS

| | | | |
|---|---|---|---|
| 5,228,701 A * | 7/1993 | Greinke et al. | 277/539 |
| 5,366,262 A * | 11/1994 | Couvreur | 285/340 |
| 5,452,082 A * | 9/1995 | Sanger et al. | 356/246 |
| 2004/0069279 A1 * | 4/2004 | Maier et al. | 123/467 |
| 2006/0273799 A1 | 12/2006 | Hunziker et al. | |
| 2007/0108378 A1 | 5/2007 | Terabayashi et al. | |
| 2007/0210530 A1 * | 9/2007 | Park et al. | 277/560 |

OTHER PUBLICATIONS

"Application Serial No. PCT/US2011/022104, Written Opinion mailed Aug. 19, 2011", 3 pgs.

* cited by examiner

OPTICAL MEASUREMENT DEVICE INCLUDING A MULTI-COMPONENT SEALING ASSEMBLY

CLAIM OF PRIORITY

This application is a U.S. National Stage Filing under 35 U.S.C. 371 from International Application No. PCT/US2011/022104 filed on Jan. 21, 2011, and published as WO 2011/094134 A2 on Aug. 4, 2011; which application claims the benefit of priority to U.S. Provisional Patent Application Ser. No. 61/298,805, entitled "OPTICAL MEASUREMENT DEVICE AND WINDOW SEALING ASSEMBLY FOR USE WITH THE DEVICE," filed on Jan. 27, 2010, which applications and publication are incorporated herein by reference in their entirety.

TECHNICAL FIELD

This patent document relates generally to optical measurement devices; and more particularly, relates to optical measurement devices and sealing assemblies intended for use at relatively high temperatures and pressures, as described herein.

BACKGROUND

Many configurations of sealing assemblies are known for providing a fluid and pressure seal between a generally transparent member forming an optical window and a supporting structure. One example of a device including such a sealing assembly is in a pressure-volume-temperature optical analysis chamber (PVT chamber), wherein one or more wavelengths of light may be directed to intersect a column of fluid under either static or dynamic conditions, in order to evaluate one or more properties of that fluid.

Some environments are particularly challenging for sealing assemblies, particularly those environments requiring operation at temperatures greater than 200 degrees Fahrenheit (F) or at pressures greater than approximately 10,000 pounds per square inch (psi). In the oil and gas industry, for example, it is often necessary or desirable to have sealing assemblies that can operate at temperatures and pressures encountered in a downhole environment, wherein the temperatures may be above 300 degrees F., and sometimes above 400 degrees F.; and wherein the pressures may be in excess of 15,000 psi, and sometimes above 20,000 psi. Even in assemblies that are not intended to be located in a downhole environment, there is often the need to simulate downhole conditions in a laboratory, and thus the sealing assemblies should be operable at the temperatures and/or pressures encountered in the subsurface environment.

BRIEF DESCRIPTION OF THE DRAWINGS

In the drawings, like numerals can be used to describe similar components throughout the several views. Like numerals having different letter suffixes can be used to represent different instances of similar components. The drawings illustrate generally, by way of example, but not by way of limitation, various embodiments discussed in the present patent document.

DETAILED DESCRIPTION

The following description refers to the accompanying drawings that depict various details of examples selected to show how the present invention may be practiced. The discussion addresses various examples of the inventive subject matter at least partially in reference to these drawings, and describes the depicted embodiments in sufficient detail to enable those skilled in the art to practice the invention. Many other embodiments may be utilized for practicing the inventive subject matter than the few illustrative examples discussed herein, and many structural and operational changes in addition to the alternatives specifically discussed herein may be made without departing from the scope of the inventive subject matter.

In this description, references to "one embodiment" or "an embodiment," or to "one example" or "an example" mean that the feature being referred to is, or may be, included in at least one embodiment or example of the invention. Separate references to "an embodiment" or "one embodiment" or to "one example" or "an example" in this description are not intended to necessarily refer to the same embodiment or example; however, neither are such embodiments mutually exclusive, unless so stated or as will be readily apparent to those of ordinary skill in the art having the benefit of this disclosure. Thus, embodiments of the present invention can include a variety of combinations and/or integrations of the embodiments and examples described herein, as well as further embodiments and examples as defined within the scope of all claims based on this disclosure, as well as all legal equivalents of such claims.

Figure 1:
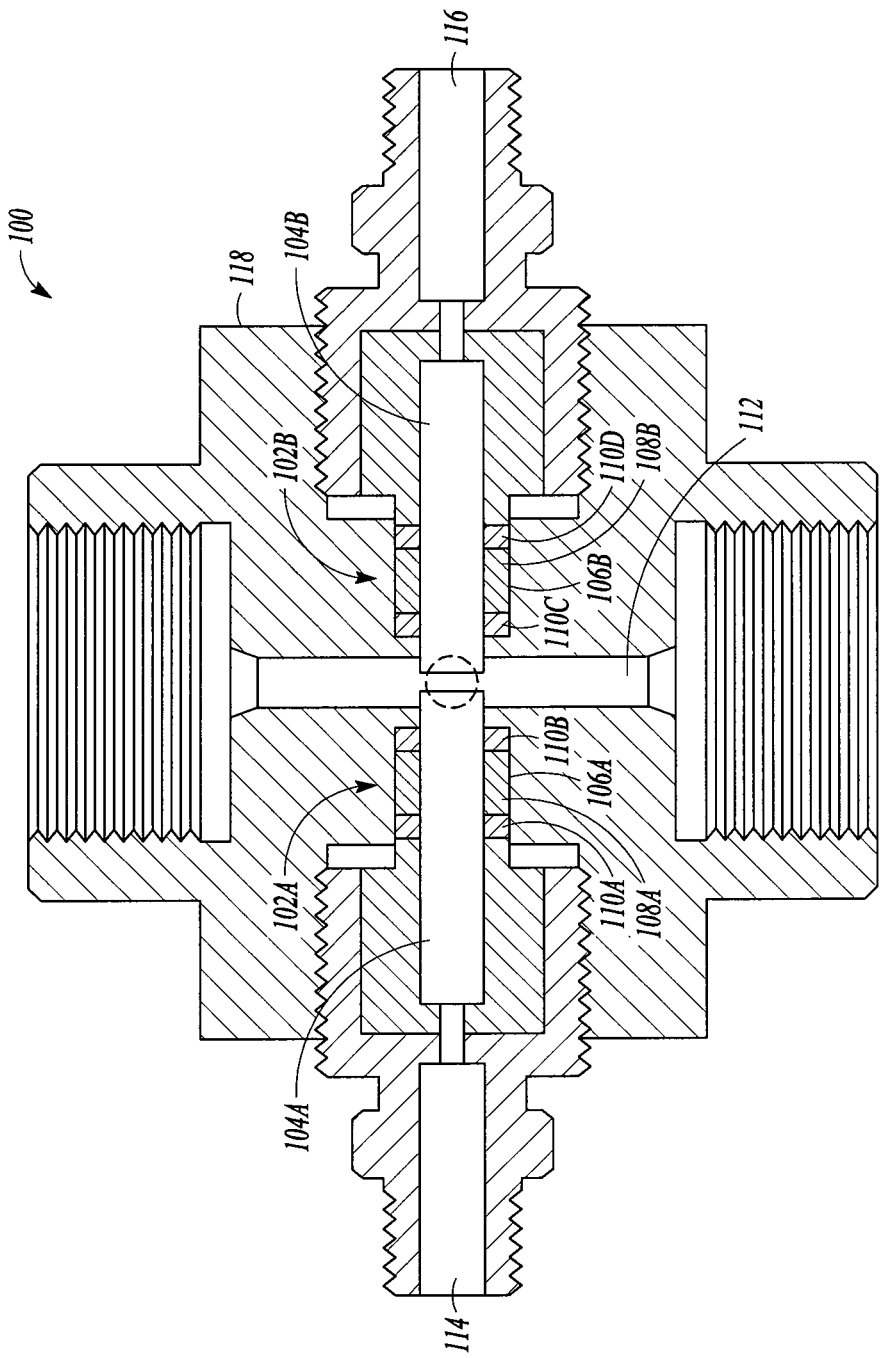
FIG. 1 depicts an optical analysis device utilizing one form of a conventional sealing assembly, illustrated from a top view and in cross section.

Referring now to the drawings in more detail, and particularly to FIG. 1, an optical analysis device 100 is illustrated from a top or plan view. The optical analysis device 100 includes a configuration of conventional sealing assemblies, generally indicated at 102A and 102B. Each sealing assembly 102A, 102B is adjacent a respective generally transparent window element 104A, 104B. Each sealing assembly 102A, 102B includes a central sleeve 108A, 108B formed of polyether ether ketone (PEEK), placed between a respective pair of O-rings 110A-B and 110C-D, which are each formed of a fluoroelastomer as marketed under the trade name VITON by DuPont Performance Elastomers, L.L.C. of Wilmington, Del., to seal between the respective window element 104A, 104B and the one or more surfaces defining the surrounding bore 106A, 106B in body member 118.

A problem experienced with these conventional sealing assemblies 102A, 102B is that they are prone to leak at pressures above 10,000 psi and/or temperatures above 200 degrees F. This tendency is exacerbated by combined high temperatures and pressures, such as those encountered in a downhole environment (either actual or simulated) as described earlier herein; and is further exacerbated by repeated exposure to these high temperatures and pressures. Another deficiency of conventional sealing assemblies 102A, 102B is that under high-stress conditions, they tend to leak if the seal assembly is cycled between different stages of loading, such as may occur by either significant changes in the fluid pressure to which the seal is subjected, or by changing the compression applied to the seal assembly as may be required to adjust the optical analysis device 100.

As will be understood by those skilled in the art, in optical analysis devices 100, a fluid can be introduced through a passageway 112, which extends between window elements 104A, 104B. Accordingly, light communicated through an input optical fiber 114 in optical communication with a first window element 104A, can pass through the fluid in passageway 112 and into the second window element 104B and an output optical fiber 116 to facilitate a desired optical measurement. The wavelength of the light directed through optical analysis device 100 can be selected in accordance with the fluid under examination and/or the property of that fluid to be evaluated, in a manner known to those skilled in the art.

Figure 2:
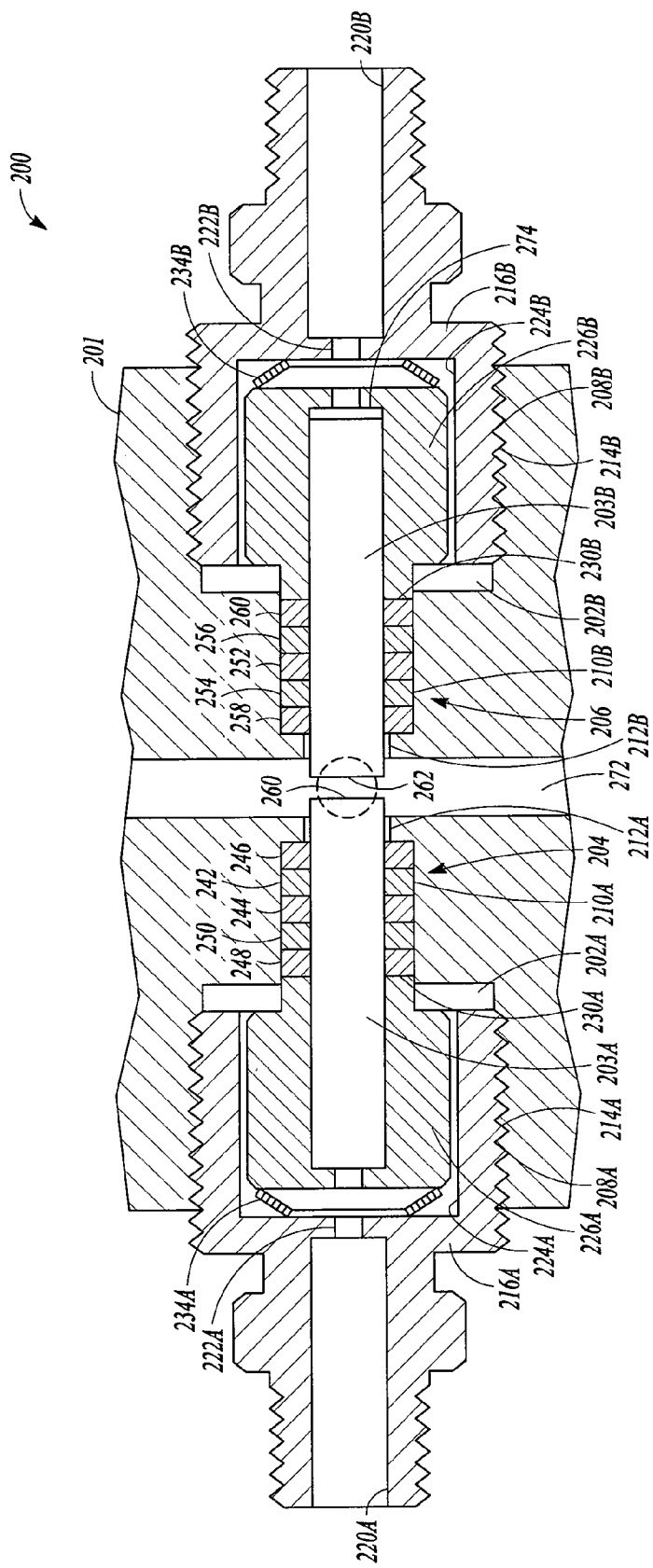
FIG. 2 depicts a portion of an optical analysis device having example sealing assemblies in accordance with various embodiments of the present invention.

Referring now to FIG. 2, a portion of an optical analysis device 200 is illustrated. The optical analysis device 200 can include a body member 201 having a plurality of bores therein, wherein two opposing bore sections, indicated generally at 202A and 202B, each house a respective seal assembly 204, 206, with the two seal assemblies being examples of two alternative configurations. As can be seen from the figure, each bore section 202A, 202B can include three aligned and coaxial bores: an outermost bore 208A, 208B (which in this example includes a threaded section 214A, 214B), a seal-receiving section 210A, 210B, and a window-receiving bore 212A, 212B, through which the respective transparent window element 203A, 203B can extend.

Each seal assembly 204, 206 can be retained within the respective seal-receiving section 210A, 210B by a retention mechanism. In the illustrated example, each retention mechanism includes a threaded coupling 216A, 216B, which threadably couples at 214A, 214B to respective threads in outermost bore 208A, 208B. Each threaded coupling 216A, 216B defines an optical fiber-receiving bore 220A, 220B, connecting through a reduced diameter passageway 222A, 222B to an inner recess 224A, 224B. A supporting block 226A, 226B can be housed within the inner recess 224A, 224B and can engage a respective seal assembly 204, 206. The above components may be formed of any desired material suitable for operation in the intended environment. In many configurations, threaded couplings 216A, 216B are formed of stainless steel, as is body member 201. Additionally, supporting blocks 226A, 226B are often formed of copper. Copper is a desirable material here because it is malleable enough to effectively distribute load on the rear of optics, and to thus maintain compression, while avoiding prevent point loading and tension on the window.

As can be seen in FIG. 2, supporting blocks 226A, 226B preferably include an inwardly-extending contact portion, which is sized to extend into the respective seal-receiving section 210A, 210B in body member 201. In some embodiments, each supporting block 226A, 226B is free to rotate within the respective inner recess 224A, 224B of the threaded coupling 216A, 216B. Each supporting block 226A, 226B can rest against the bottommost surface defining each inner recess 224A, 224B, such that threading of threaded coupling 216A, 216B pushes directly against the supporting block 226A, 226B, and through contact portion 230A, 230B to apply loading to the respective seal assembly 204, 206. However, in some embodiments, it is preferable to include a loading mechanism, such as a Belleville spring 234A, 234B, between each threaded coupling 216A, 216B and the respective supporting block 226A, 226B, which establishes a preload force on the respective seal assembly 204, 206. In other embodiments, it is preferable to omit the Belleville spring, for example, to allow direct control of the loading on the seal assembly through the engagement positioning. The ability of each supporting block 226A, 226B to rotate relative to its respective threaded coupling 216A, 216B serves to decouple rotation of the threaded coupling 216A, 216B (when the components are assembled or adjusted), from being applied to the seal assembly 204, 206.

Turning now to the seal assemblies 204, 206, each seal assembly can be formed of a plurality of elements offering distinct capabilities to the overall seal assembly. Addressing seal assembly 204, it can include a relatively deformable seal component to fully engage and seal between window member 203A, and the one or more surfaces defining the surrounding bore 210A. One suitable material for this relatively deformable component is an O-ring 242, or a similarly formed continuous packing member, formed of a fluoroelastomer, marketed under the trade name AFLAS, by AGC Chemicals Americas, Inc., and/or Seals Eastern, Inc. of Read Bank, N.J. Applicants understand that AFLAS is based on an alternating copolymer of tetrafluoroethylene and propylene, along with fillers, curatives, and other agents. The AFLAS is generally chemically inert, and offers excellent heat resistance to temperatures over 400 degrees F. However, being of a relatively flexible composition, under extremes of pressure as described herein, the AFLAS seal element may tend to cold flow and to thereby lose some of its sealing functionality.

In order to support the AFLAS seal element in such a way that it maintains its sealing functionality, seal assembly 204 can provide at least one backup seal element 244, 246 located on each side of the AFLAS O-ring 242. These backup seal elements 244, 246 also need to offer stability at high temperatures, and must be sufficiently stable at such temperatures and pressures as to support O-ring 242 sufficiently to prevent cold flow of the O-ring. One suitable material for these backup seal elements is a flexible graphite material marketed under the trade name GRAFOIL, by GrafTech International, of Lakewood, Ohio. The GRAFOIL seal elements can be constructed in various ways, such as being stamped out of a relatively thick sheet of the material, or alternatively, a continuous ribbon of the material can be wrapped around the desired location (or around a forming mandrel) to build up a seal member of the needed dimension. As an alternative to the described GRAFOIL backup seal elements, other materials might be used, such as soft metals, for example, Indium foil or an Indium gasket. Other soft metals could also be utilized. Additionally, as an alternative to the AFLAS seal element, a different material might be utilized, for example, polytetrafluoroethylene (PTFE), which is best known by the DuPont brand name TEFLON; or in some cases, a ring formed of VITON, as described earlier herein.

The example seal assembly 204 can further include seal elements 248 and 250 on the end away from the fluid channel 272. One element 250 is located adjacent backup seal element 244 and is preferably formed of GRAFOIL flexible graphite, or another material offering similar properties, as discussed above. Outermost element 248 is selected for both temperature stability and relatively high resistance to wear (which may occur in the event of rotation of the support member), and may be formed, for example, of a polyether ether ketone (PEEK).

Seal assembly 206 can be of a different configuration than seal assembly 204. Seal assembly 206 again can include a central seal element 252, which may be formed of AFLAS, or potentially another material, as discussed above; and again can include backup elements 254, 256 on either side of central seal element 252; such those formed of GRAFOIL flexible graphite, or potentially another material, as discussed above. However, in seal assembly 206, both of the outermost elements 258, 260 can be formed of PEEK (or another material with similar properties), to provide protection from abrasion for GRAFOIL backup element 256, and to provide protection against erosion for GRAFOIL backup element 254, which would otherwise be directly exposed to movement of fluid through passageway 272. Additionally, PEEK can be formed to serve as an extrusion barrier for the GRAFOIL elements.

In the course of the optical analysis of a fluid, it may be desirable to change the spacing gap between the innermost surfaces 260, 262 of the windows 203A, 203B. For example, as can be seen in FIG. 2, the right-hand side window 203B is not fully seated at the back of recess 274 in supporting block 226B. As noted previously, one problem with conventional seal assemblies is that once they seal at elevated temperatures and pressures, if the loading on the seal assembly is relaxed, the seal will leak, in part due to deformation of one or more components in the assembly; and in many cases, the leak will persist even after the seal is again compressed. However, the multi-component seal assembly described herein can be constructed to offer improved performance which will allow loading on the seal to be cycled through multiple iterations of compression and relative relaxation. This capability of spacing gap adjustment allows additional functionality in the optical measurement device of the capability of relaxing the compression on one of the seal assemblies slightly (by loosening the threaded coupling 216B) to allow the window 203B to move relative to seal assembly 206, and to thus change the gap between the two windows.

One problem that can be encountered with optical measurement devices that include a transparent window is that, in some cases, light may be reflected from the material surrounding the window, thereby "contaminating" the spectral signature of the material (here, the sample fluid flowing in passageway 272), with the spectral signature of materials adjacent the window, such as, in this example, seal assemblies 204 and 206. Accordingly, in some embodiments of optical measurement devices in accordance with this disclosure, it is preferable to place a reflective material around the sides of the window to provide an optical barrier isolating the window from the surrounding materials. The material usually only needs to be generally reflective, and only at the wavelengths of light with which the system will be used. In systems or devices in which visible light will be used, Quartz, or sometimes glass is a suitable window material. Additionally, the windows do not always have to be a single crystal, but in some cases may be able to be formed of a glass fiber rod or fiber bundle.

Embodiments for use within the oil and gas industry frequently need to operate through use of a relatively wide range of wavelengths of light, ranging from approximately 200 nanometers (nm) to 6000 nm, with many desirable systems or devices operating in a slightly narrower range of from approximately 400 nm to 5500 nm. For these types of systems or devices, a sapphire window is satisfactorily transparent within these ranges of wavelengths, although zinc sulfide or zinc selenide may be suitable for some devices. For many of these applications, gold is a suitable reflective material for light in the infrared (IR) spectrum. In some examples, particularly involving light in the visible spectrum, aluminum or silver may be used as the reflective material. In some examples, the reflective material is implemented as a coating bonded to the exterior surface of the window. One way of forming this coating is to sputter coat the gold onto the window (leaving the ends uncoated), and to then fire the sputter coated rod in a furnace to facilitate bonding between the gold and sapphire. For example, firing a coated window at approximately 1300 degrees C. for approximately 30 minutes has been found to be sufficient to achieve the desired bonding.

Figure 3:
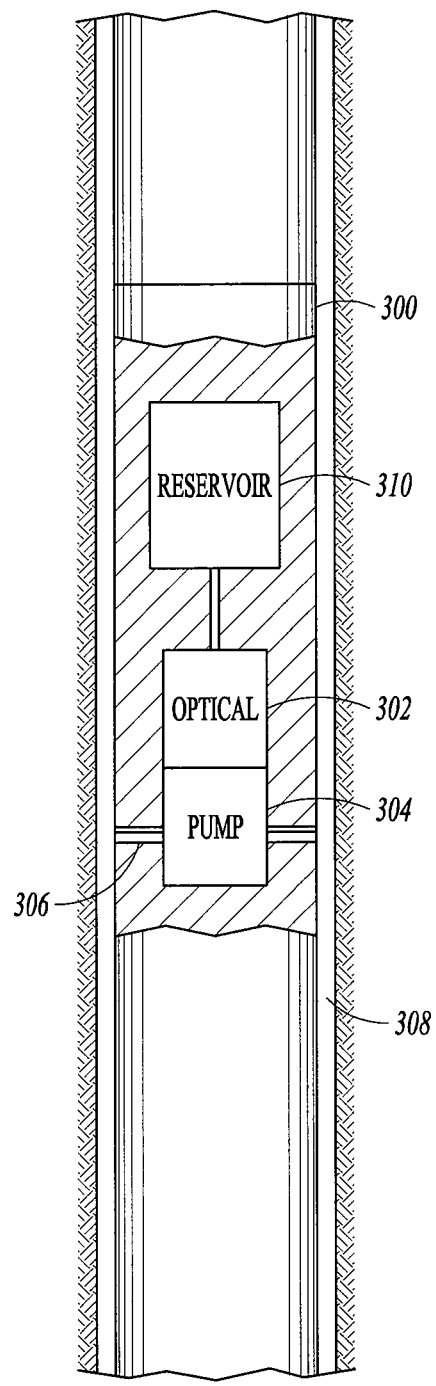
FIG. 3 depicts a block diagram of an example logging tool including an optical analysis device in accordance with various embodiments of the present invention.

FIG. 3 depicts a portion of a well logging tool 300 including an optical analysis device 302, as described above. As will be apparent to those skilled in the art, many types of well logging tools may incorporate an optical analysis device that includes at least one optical window and sealing assembly similar to those discussed above. In the example of FIG. 3, the well logging tool 300 includes a pump 304, which is selectively coupled through passageways 306 which extend to the annulus surrounding the tool. Pump 304 can be actuated to draw fluid from the annulus into the tool, and to be pumped through optical analysis device 302. From there, the fluid can, in this example, be retained in a reservoir 310 for further analysis at the surface. The well logging tool 300 can be either a measurement-while-drilling (MWD) tool, or may be wireline conveyed, as is well known to those skilled in the art. In either event, the well logging tool 300 can include a housing 308 containing the described components and configured for attachment and communication with other tools are components as necessary; and can also include appropriate control and communication systems to control the functioning of the tool and communication with the tool in a desired manner.

To better illustrate the devices and tools described herein, a non-limiting list of examples is provided here:

In Example 1, an optical measurement device comprises a body member including one or more surfaces defining an aperture; an optical window disposed at least partially within the aperture; and a multi-component seal assembly extending between and engaging the optical window and the one or more surfaces defining the aperture. The multi-component seal assembly comprises a deformable seal element, at least one backup seal element on each side of the deformable seal element, and at least one additional seal element functioning as an extrusion barrier on the opposite side of one or both backup seal elements from the deformable seal element.

In Example 2, the optical measurement device of Example 1 is optionally configured such that the backup seal elements are each formed of a material that is resistant to cold flow at temperatures up to about 350 degrees F., and at pressures up to about 15,000 psi.

In Example 3, the optical measurement device of any one of Examples 1 or 2 is optionally configured such that the backup seal elements are each formed of a material selected from a group consisting of flexible graphite or Indium metal.

In Example 4, the optical measurement device of Example 3 is optionally configured such that the backup seal elements are stamped out of a sheet of the material or include a continuous ribbon of the material.

In Example 5, the optical measurement device of any one of Examples 1-4 is optionally configured such that the multi-component seal assembly includes at least two backup seal elements on either side of the deformable seal element.

In Example 6, the optical measurement device of any one of Examples 1-5 is optionally configured such that the deformable seal element is formed of a material selected from a group consisting of a fluoroelastomer or polytetrafluoroethylene.

In Example 7, the optical measurement device of Example 6 is optionally configured such that the deformable seal element is formed of a copolymer including tetrafluoroethylene and propylene.

In Example 8, the optical measurement device of any one of Examples 1-7 is optionally configured such that the at least one additional seal element includes two seal elements on the opposite side of one or both backup seal elements from the deformable seal element.

In Example 9, the optical measurement device of any one of Examples 1-8 is optionally configured such that the at least one additional seal element includes a seal element on the opposite side of each backup seal element from the deformable seal element.

In Example 10, the optical measurement device of any one of Examples 1-9 is optionally configured such that the at least one additional seal element is formed of a material selected from a group consisting of polyether ether ketone or flexible graphite. In Example 11, the optical measurement device of any one of Examples 1-10 is optionally configured such that the optical window is formed from a material selected from a group consisting of sapphire, zinc sulfide, or zinc selenide.

In Example 12, the optical measurement device of any one of Examples 1-11 optionally further comprises a reflective material placed around one or more sides of the optical window providing an optical barrier.

In Example 13, the optical measurement device of Example 12 is optionally configured such that the reflective material is selected from a group consisting of gold, aluminum, or silver.

In Example 14, the optical measurement device of any one of Examples 12 or 13 is optionally configured such that the reflective material is coated onto an exterior surface of the optical window.

In Example 15, the optical measurement device of any one of Examples 1-14 optionally further comprises a supporting block including a recess for receiving a portion of the optical window, and wherein an outermost surface of the optical window is not fully seated against the back of the recess allowing an innermost surface of the optical window to be adjusted outward during optical analysis of a fluid.

In Example 16, the optical measurement device of any one of Examples 1-15 optionally further comprises a deformable loading mechanism positioned between a portion of a retention mechanism and a supporting block disposed within a recess of the retention mechanism.

In Example 17, a well logging tool configured for use in an Earth borehole comprises a housing and an optical measurement device contained in the housing. The optical measurement device includes elements selected from any one of Examples 1-16.

In Example 18, a testing device comprises a body member including one or more surfaces defining an aperture; an optical window extending within the aperture; and a sealing assembly configured for use at pressures greater than 10,000 psi and at temperatures greater than 200 degrees F. The sealing assembly extends between the optical window and the one or more aperture-defining surfaces, and comprises a first seal member formed of a material selected from a group consisting of a fluoroelastomer or polytetrafluoroethylene, a second seal member formed of either flexible graphite or a metal foil, and a third seal member formed of either flexible graphite or a metal foil, wherein the second and third seal members are on opposite sides of the first seal member.

In Example 19, the testing device of Example 18 optionally further comprises at least one additional seal member functioning as an extrusion barrier, and is placed adjacent to either the second or third seal member.

In Example 20, the testing device of Example 19 is optionally configured such that the at least one additional seal member is formed of a material selected from a group consisting of polyether ether ketone or flexible graphite.

In Example 21, the testing device of any one of Examples 18-20 includes a sealing assembly configured for use at pressures up to about 15,000 psi and at temperatures up to about 300 degrees F.

In Example 22, the testing device of any one of Examples 18-21 includes a sealing assembly configured for use at pressures up to about 20,000 psi.

In Example 23, the testing device of any one of Examples 18-22 includes a sealing assembly configured for use at temperatures up to about 400 degrees F.

In Example 24, the optical measurement device, well logging tool, or test device of any one or any combination of Examples 1-23 is optionally configured such that all elements or options recited are available to use or select from.

Many modifications and variations may be made to the techniques and structures described herein without departing from the scope of the present invention. For example, the alternative materials described herein is not necessarily an exhaustive list, and for many applications, even including those at elevated temperatures and pressures, other combinations of materials may be found that will perform satisfactorily.

In the appended claims, the terms "including" and "in which" are used as the plain-English equivalents of the respective terms "comprising" and "wherein." Also, in the following claims, the terms "including" and "comprising" are open-ended, that is, a system, assembly, device, apparatus, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The following claims are hereby incorporated into the Detailed Description, with each claim standing on its own as a separate embodiment. The scope of the invention should be determined with reference to the appended claims, along with the full scope of equivalents to which such claims are entitled.

The Abstract is provided to comply with 37 C.F.R. §1.72 (b), to allow the reader to quickly ascertain the nature of the present patent document. It is submitted with the understanding that it will not be used to interpret or limit the scope or meaning of the claims.

We claim:

1. An optical measurement device, comprising:
    a body member including one or more surfaces defining an aperture;
    an optical window disposed at least partially within the aperture; and
    a multi-component seal assembly extending between and engaging the optical window and the one or more surfaces defining the aperture, comprising,
        a deformable seal element,
        at least one backup seal element positioned on each side of, and directly contacting, the deformable seal element, and
        at least one additional seal element positioned on the opposite side of one or both backup seal elements from the deformable seal element, the at least one additional seal element directly contacting the opposite side of one or both backup seal elements.

2. The optical measurement device of claim 1, wherein the backup seal elements are each formed of a material that is resistant to cold flow at temperatures up to about 350 degrees F., and at pressures up to about 15,000 psi.

3. The optical measurement device of claim 1, wherein the backup seal elements are each formed of a material selected from a group consisting of flexible graphite or Indium metal.

4. The optical measurement device of claim 3, wherein the backup seal elements are stamped out of a sheet of the material or include a continuous ribbon of the material.

5. The optical measurement device of claim 1, wherein the multi-component seal assembly includes at least two backup seal elements positioned on either side of the deformable seal element.

6. The optical measurement device of claim 1, wherein the deformable seal element is formed of a material selected from a group consisting of a fluoroelastomer or polytetrafluoroethylene.

7. The optical measurement device of claim 6, wherein the deformable seal element is formed of a copolymer including tetrafluoroethylene and propylene.

8. The optical measurement device of claim 1, wherein the at least one additional seal element includes two seal elements positioned on the opposite side of one or both backup seal elements from the deformable seal element.

9. The optical measurement device of claim 1, wherein the at least one additional seal element includes a seal element positioned on the opposite side of each backup seal element from the deformable seal element.

10. The optical measurement device of claim 1, wherein the at least one additional seal element is formed of a material selected from a group consisting of polyether ether ketone or flexible graphite.

11. The optical measurement device of claim 1, wherein the optical window is formed from a material selected from a group consisting of sapphire, zinc sulfide, or zinc selenide.

12. The optical measurement device of claim 1, further comprising a reflective material placed around one or more sides of the optical window providing an optical barrier.

13. The optical measurement device of claim 12, wherein the reflective material is selected from a group consisting of gold, aluminum, or silver.

14. The optical measurement device of claim 12, wherein the reflective material is coated onto an exterior surface of the optical window.

15. The optical measurement device of claim 1, further comprising a supporting block including a recess for receiving a portion of the optical window, and wherein an outermost surface of the optical window is not fully seated against the back of the recess allowing an innermost surface of the optical window to be adjusted outward during optical analysis of a fluid.

16. The optical measurement device of claim 1, further comprising a deformable loading mechanism positioned between a portion of a retention mechanism and a supporting block disposed within a recess of the retention mechanism.

17. A well logging tool configured for use in an Earth borehole, comprising:
a housing; and
the optical measurement device of claim 1, contained in the housing.

18. A testing device, comprising:
a body member including one or more surfaces defining an aperture;
an optical window extending within the aperture; and
a sealing assembly configured for use at pressures greater than 10,000 psi and at temperatures greater than 200 degrees F., the sealing assembly extending between the optical window and the one or more aperture-defining surfaces, and comprising,
a first seal member formed of a material selected from a group consisting of a fluoroelastomer or polytetrafluoroethylene,
a second seal member and a third seal member formed of either flexible graphite or a metal foil, the second and third seal members positioned on opposite sides of, and directly contacting, the first seal member, and
at least one additional seal member positioned adjacent to, and directly contacting, either the second seal member or the third seal member.

19. The testing device of claim 18, wherein the at least one additional seal member is formed of a material selected from a group consisting of polyether ether ketone or flexible graphite.

20. The testing device of claim 18, wherein the sealing assembly is configured for use at pressures up to about 15,000 psi and at temperatures up to about 300 degrees F.

21. The testing device of claim 18, wherein the sealing assembly is configured for use at pressures up to about 20,000 psi.

22. The testing device of claim 18, wherein the sealing assembly is configured for use at temperatures up to about 400 degrees F.

* * * * *